US010590448B2

(12) United States Patent
Benjamins et al.

(10) Patent No.: US 10,590,448 B2
(45) Date of Patent: Mar. 17, 2020

(54) PRODUCTION OF GALACTO-OLIGOSACCHARIDES

(71) Applicant: FrieslandCampina Nederland B.V., Amersfoort (NL)

(72) Inventors: Frédéric Benjamins, Amersfoort (NL); Linqiu Cao, Amersfoort (NL); Antonius Augustinus Broekhuis, Groningen (NL)

(73) Assignee: Friesland Campina Nederland B.V., Amersfoort (NL)

( * ) Notice: Subject to any disclaimer, the term of this patent is extended or adjusted under 35 U.S.C. 154(b) by 273 days.

(21) Appl. No.: 14/915,683

(22) PCT Filed: Sep. 4, 2014

(86) PCT No.: PCT/NL2014/050604
§ 371 (c)(1),
(2) Date: Mar. 1, 2016

(87) PCT Pub. No.: WO2015/034356
PCT Pub. Date: Mar. 12, 2015

(65) Prior Publication Data
US 2016/0194675 A1 Jul. 7, 2016

(30) Foreign Application Priority Data
Sep. 5, 2013 (EP) .................... 13183222

(51) Int. Cl.
| C12P 19/04 | (2006.01) |
| C12P 19/14 | (2006.01) |
| C07H 3/06 | (2006.01) |
| C07H 1/00 | (2006.01) |
| C13K 5/00 | (2006.01) |
| C12P 19/00 | (2006.01) |
| C12N 11/08 | (2020.01) |
| C12N 9/38 | (2006.01) |

(52) U.S. Cl.
CPC ............. *C12P 19/04* (2013.01); *C07H 1/00* (2013.01); *C07H 3/06* (2013.01); *C12N 9/2471* (2013.01); *C12N 11/08* (2013.01); *C12P 19/00* (2013.01); *C12P 19/14* (2013.01); *C12Y 302/01023* (2013.01); *C13K 5/00* (2013.01)

(58) Field of Classification Search
None
See application file for complete search history.

(56) References Cited

U.S. PATENT DOCUMENTS

| 6,177,109 | B1 * | 1/2001 | Hidaki | ........... A21D 8/042 426/20 |
| 7,166,451 | B1 | 1/2007 | Yang | |

FOREIGN PATENT DOCUMENTS

| EP | 0168127 A2 | 1/1986 |
| JP | 03-216185 A | 9/1991 |
| JP | 03-277276 A | 12/1991 |
| RU | 2108044 C1 * | 4/1998 |

OTHER PUBLICATIONS

Warmerdam, A. "Synthesis of galacto-oligosaccharides with β-galactosidases", Ph.D. Thesis, Wageningen University, Wageningen, NL, Jun. 2013 (Year: 2013).*
Vera et al., Enzyme Microb. Technol. 50:188-194, 2012 (Year: 2012).*
Neri et al., Food Chem. 115:92-99, 2009 (Year: 2009).*
Huzjak et al. (Prehrambeno-technol. Biotechnol. Rev. 32:177-179, 1994 (Year: 1994).*
DFE pharma Product Specification for Lactochem® Lactose Monohydrate, Jan. 2016, 2 pages (Year: 2016).*
English translation of JP 03-216185 A, Oct. 2018, 19 pages (Year: 2018).*
Hughes, C. "Galactooligosaccharide supplementation reduces stress-induced gastrointenstinal dysfunction and days of cold or flu: a randomized, double-blind, controlled trial in healthy university students", Thesis, University of Florida, Gainesville, FL, 2011 (Year: 2011).*
Coulier et al., "In-Depth Characterization of Prebiotic Galacto-oligosaccharides by a Combination of Analytical Techniques", Journal of Agricultural and Food Chemistry, vol. 57, pp. 8488-8495; 2009.
Warmerdam et al., "Characterization of Beta-Galactosidase Isoforms from Bacillus circulans and Their Contribution to GOS Production", Appl Biochem Biotechnol., vol. 170, pp. 340-358; 2013.
Grosova et al., Perspectives and Applications of Immobilised Beta-Galactosidase in Food Industry—a Review, Czech J. Food Sci., vol. 26, No. 1, pp. 1-14; 2008.
Gaur et al., "Galacto-oligosaccharide synthesis by immobilized Aspergillus oryzae Beta-galactosidase", Food Chemistry, vol. 97, pp. 426-430; 2006.
Torres et al., Galacto-Oligosaccharides: Production, Properties, Applications, and Significance as Prebiotics, Comprehensive Reviews in Food Science and Food Safety, vol. 9, pp. 438-454; 2010.
Cao et al., "Immobilized Enzymes", Elsevier B.V., pp. 461-475; 2011.
Rivera-Urgell et al., "Oligosaccharides: application in infant food", Early Human Development, vol. 65, pp. S43-S52; 2001.
Panesar et al., "Microbial Production, Immobilization and Applications of Beta-D-Galactosidase", Journal of Chemical Technology and Biotechnology, vol. 81, pp. 530-543; 2006.
Urrutia et al., "Immobilization of Bacillus circulans Beta-galactosidase and its application in the synthesis of galacto-oligosaccharides under repeated-batch operation", Biochemical Engineering Journal, vol. 77, pp. 41-48; 2013.

(Continued)

Primary Examiner — David Steadman
(74) Attorney, Agent, or Firm — Hoffmann & Baron, LLP

(57) ABSTRACT

The invention relates to the enzymatic preparation of galacto-oligosaccharides (GOS). Provided is a method for preparing GOS from lactose, comprising (i) contacting a lactose feed with immobilized beta-galactosidase (EC 3.2.1.23) and (ii) allowing for GOS synthesis, wherein said lactose feed is an aqueous slurry of crystalline lactose.

14 Claims, 2 Drawing Sheets

(56) References Cited

OTHER PUBLICATIONS

Palai et al., "Kinetics of Lactose Conversion to Galacto-Oligosaccharides by [Beta]-Galactosidase Immobilized on PVDF Membrane", Journal of Bioscience and Bioengineering, vol. 115, No. 6, pp. 668-673; 2013.
Benjamins et al., "Assessment of Repetitive Batch-Wise Synthesis of Galacto-Oligosaccharides from Lactose Slurry Using Immobilised [Beta]-Galactosidase from Bacillus Circu", International Dairy Journal, vol. 38, No. 2, pp. 160-168; 2014.
Panesar, et al., "Review: Microbial production, immobilization and applications of β-D-galactosidase," J. Chem. Technol. Biotechnol., pp. 530-543, vol. 81 (2006).
Notification of Reason(s) for Refusal, Patent Application No. 2016-540836, 10 pages, dated Jul. 10, 2018.

\* cited by examiner

PRODUCTION OF GALACTO-OLIGOSACCHARIDES

This application is the U.S. National Phase of, and Applicants claim priority from, International Patent Application Number PCT/NL2014/050604 filed Sep. 4, 2014, which claims priority from EP 13183222.2 filed Sep. 5, 2013, each of which is incorporated herein by reference.

The invention relates to methods for preparing galacto-oligosaccharides (GOS). GOS, also known as oligogalactosyllactose, oligogalactose, oligolactose or transgalactooligosaccharides (TOS), is an important food ingredient [1]. Because of its indigestible nature, GOS belongs to the group of prebiotics. Prebiotics are defined as non-digestible food ingredients that beneficially affect the host by stimulating the growth and/or activity of beneficial bacteria in the colon. The ability of GOS, when added to infant milk formulas, to replicate the bifidogenic effect of human milk, not only in bacterial numbers, but also with respect to the metabolic activity of the colonic microbiota, has significantly increased interest in their production and application in various food and pharmaceutical processes. For example, GOS occurs in commercial available products such as food for both infants and adult, ranging from infant formula to food for the critical ill.

As its name suggests, the GOS synthesis typically involves a number of galactosyl transfer processes catalyzed by β-galactosidase (β-D-galactohydrolase; EC 3.2.1.23), which uses lactose as galactosyl donor and lactose or the intermediate GOS species as galactosyl acceptor.

The underlying mechanism is depicted in Scheme 1. In short, the enzyme and the galactosyl donor (lactose, β-D-Galp-(1,4)-β-D-Glcp) initially form a transient galactosyl-enzyme complex (En-Galp) and subsequently a true covalent galactosyl-enzyme complex (En-Galp), which releases a glucose (molecule (β-D-Glcp) from the complex. Then, another galactosyl acceptor (lactose, β-D-Galp-(1,4)-β-D-Glcp or other GOS species) binds to the complex in the active center and performs a nucleophilic attack on this galactosyl-enzyme complex (En-Galp) generally with its non-reducing end (galactosyl moiety of lactose), thus resulting in the formation of a DP3 GOS species, which is expressed generally as β-D-Galp-(1→n)-β-D-Galp-(1,4)-β-D-Glcp products, where the n represents the position of the glycoside linkage, which can be 2, 3, 4, or 6, depending on the source of the enzyme and the applied reaction conditions.

Scheme 1 Schematic depiction of the GOS synthesis mechanism by β-galactosidase-catalyzed elongation of lactose by β-1,4 glycosidic linkages.

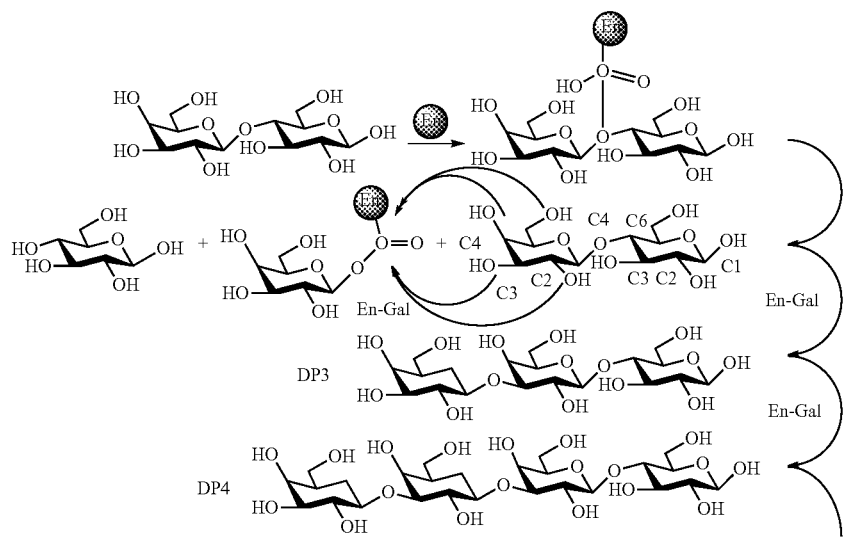

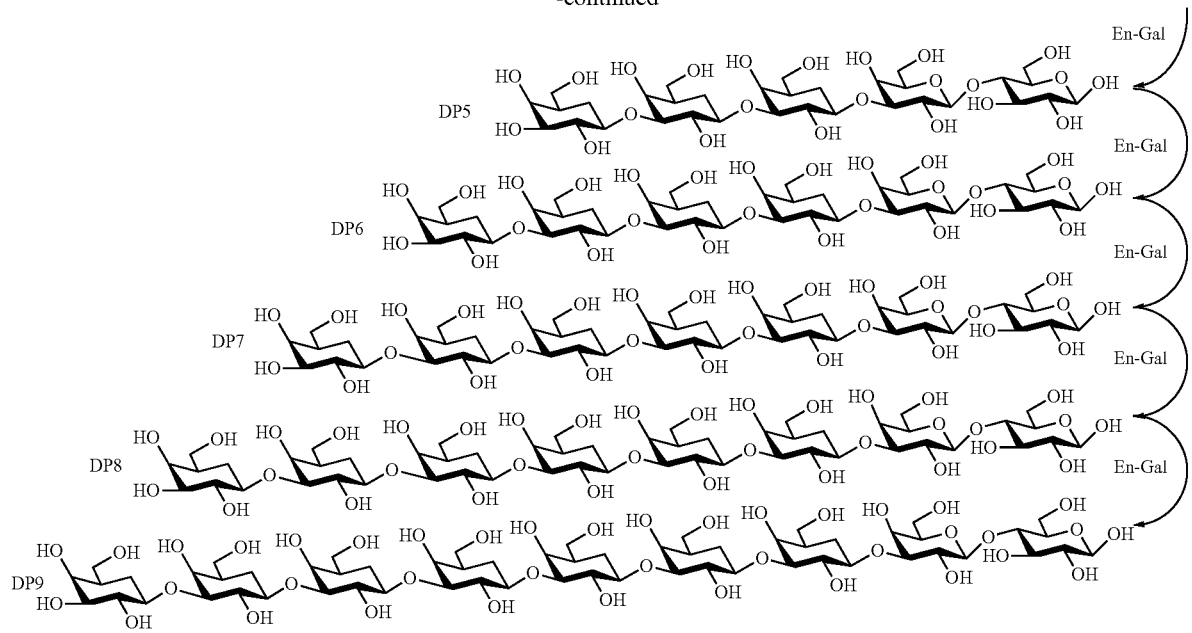

As the reaction progresses (see Scheme 1), more and more galactosyl moieties are transferred to the existing GOS species, leading to the formation of GOS species with different degree of polymerization (DP). Therefore, the GOS can be generally expressed as (Gal)m-Glc (where m varies usually between 2-9, depending on the source of the enzyme and the reaction conditions applied). Apart from the ≥DP3 GOS species, new DP2 species such as allolactose are usually considered as the primary product of the transgalactosylation action of β-galactosidase. These new DP2 species formed by the transgalactosylation of β-galactosidase can further take part in the formation of higher DP GOS species, thus complicating the GOS product spectrum, as discussed below.

Although the enzyme β-galactosidase has numerous applications in the food and dairy industries, the moderate stability of enzyme is one of the limitations that hinder general implementation of biocatalysts at an industrial scale. Studies to explore their full potential as catalyst have resulted in various suitable strategies for enzyme stabilization. For example, the enzyme has been immobilized by various methods such as physical absorption, entrapment, and covalent binding method on different supports. Immobilization has also shown to have an advantageous effect on reducing production inhibition of β-galactosidase. Still further, enzyme immobilization facilitates enzyme reusability and continuous operation of the GOS synthesis process.

It is well known that β-galactosidase-catalyzed GOS synthesis is kinetically controlled [2]. This means that the actual amount of galacto-oligosaccharide formed at a certain point in time depends largely on the relative rates of the desired synthetic reactions versus and the undesired hydrolytic reactions of lactose and/or GOS. This, in turn, depends not only on the lactose concentration but also on the GOS species that are formed, and moreover, on the interaction of the enzyme with the products resulting from the synthesis and the hydrolysis.

Thus, the various GOS species can be used not only as acceptors for further GOS synthesis but also as substrates for hydrolysis. The hydrolytic reaction will dominate generally at the later stages of the reaction when the peak in GOS concentration has passed and the main substrate lactose concentration in the reaction mixture is decreased to a low value. On the other hand, production inhibition may also occur, when more and more products accumulate, resulting in either the inhibition of GOS synthesis or GOS hydrolysis.

Various factors are know in the art to increase the yield of GOS synthesis from lactose using β-galactosidase. See Torres et al. for a review on the production, the properties and the applications of GOS. The reaction conditions for transgalactosylation should be high lactose concentration, elevated temperature, and low water activity in the reaction medium. The temperature, concentration of substrate, and enzyme origin play an important role in the enzymatic synthesis of oligosaccharides. However, the influence of the initial lactose concentration can be much larger. Regarding the use of highly concentrated starting lactose solution, it has been shown that maximum GOS yield is largely influenced by initial lactose concentration mainly, until the concentration range is 30% to 40% (w/v). In general, more and larger galacto-oligosaccharides (GOSs) can be produced with higher initial lactose concentrations. Since lactose solubility is relatively low at room temperature but manifestly increases with increasing temperature, high temperatures are generally desired.

The higher temperatures can be beneficial in higher oligosaccharide yields. The higher yield at higher temperatures is an additional advantage when operating at high initial lactose concentrations and, consequently, elevated temperatures. On the other hand, the potentials of immobilized beta-galactosidase for the synthesis of GOS, e.g. reducing the cost contribution of the enzyme by efficient recycling, easy handing and process control and enabling a continuous process have been widely recognized. However, the industrial use of immobilized beta-galactosidase for the production of GOS has been not reported yet. In the example of the study by Urretia et al., it was shown that immobilized B. circulans β-galactosidase was recyclable, when performing the reaction at 60° C. in a 50% (w/w) lactose solution using a high enzyme dosage (~18% of the lactose (w/w)) under repeated batch operation.

Consequently, GOS synthesis is generally preferred to be performed using immobilized enzyme under conditions with a high initial lactose concentration in order to achieve a high GOS yield and to reduce the hydrolytic side reaction [3,4,5].

However, the present inventors found that the results obtained from optimization studies performed in a research setting do not always provide a good indicator for GOS synthesis at an industrial scale, e.g. in food industries, wherein relatively low enzyme concentrations (and/or a smaller volume of immobilized enzyme) and long (>20 hours) incubation periods that are typically used for economical reasons, in order to achieve a high productivity and a high space-time yield. In particular, they observed that the use of a highly concentrated (55% w/w) lactose solution as lactose feed for GOS synthesis at 60° C. in a repeated batch operation resulted in a loss of about 95% of the initial activity LU of the immobilized enzyme after the second cycle of operation.

Therefore, they set out to develop improved reaction conditions for GOS synthesis at an industrial scale which allows for repeated re-usage of immobilized enzyme while retaining substantial enzyme activity and without sacrificing a high GOS yield and a cost-effective operation.

It was surprisingly found that the above goals could be met by using a slurry of crystalline lactose instead of a highly concentrated solution of dissolved lactose as a lactose feed. More specifically, 20% of the initial LU enzyme activity (measured as LU as defined below) was retained after the third reaction cycle when a lactose slurry of 55% w/w was incubated with immobilized enzyme at 58° C. for 24 hours. The final GOS content was above 60% (dm) during the initial six batches. Without wishing to be bound by any theory, it is speculated that a conventional highly concentrated lactose solution prepared by complete dissolution at high temperature, is to be considered as a "meta stable" solution,) that will undergo recrystallization at a lower reaction temperature during prolonged incubation periods. This causes lactose crystal formation on the surface and in the pores of the enzyme carrier, presumably leading not only to a reduced accessibility but also to inactivation (denaturation) of the immobilized enzyme. Surprisingly, this can be avoided by using a suspension of "pre-crystallized" lactose wherein the lactose crystals function as a substrate pool and the dissolved lactose can freely access the pores of the enzyme carrier. Thus, the enzyme denaturation can be retarded by the use of "pre-crystallized" lactose, without the need to dissolve lactose completely by pre-heating the crystallized lactose to a higher temperature, thus resulting in a sustainable industrial process.

Accordingly, the invention provides a method for preparing galacto-oligosaccharides (GOS) from lactose, comprising contacting a lactose feed with β-galactosidase which is immobilized, preferably on a solid carrier, and allowing for GOS synthesis, wherein said lactose feed is an aqueous slurry of crystalline lactose.

As used herein, the term "aqueous slurry" refers to a watery mixture (suspension) of insoluble lactose crystals i.e. a composition wherein not all lactose is dissolved and wherein the soluble lactose concentration is equal to its solubility at a given reaction temperature. As indicated above, lactose solubility is strongly dependent on the temperature. FIG. 1 shows the solubility-temperature relation for lactose in water at neutral pH.

Typically, the aqueous lactose slurry for use in the present invention contains 17%-75% (w/w) lactose. In practice, a high lactose content in the slurry may result in a concentrated product in the reactor that requires less energy to further concentrate to obtain the finished GOS syrup of 75% (w/w). Therefore, both for economical reason and very good GOS yields, the lactose slurry is preferred to contain 50-70% (w/w) lactose in total. For example, the aqueous lactose slurry contains at least 53% (w/w), preferably at least 55% (w/w) lactose. By increasing the total dry matter content of the reaction mixture without sacrificing enzyme stability, the method of the invention provides a very high productivity and GOS output per reactor volume.

A slurry for use in the present invention is easily prepared by adding crystalline lactose (monohydrate) to an aqueous liquid. The skilled person will be able to calculate the lactose concentration needed to obtain a slurry at a given temperature based on the lactose solubility curve. For example, the following empiric equation can be used to calculated soluble lactose at a given reaction temperature (T):

$$\text{solubility of lactose} = 0.003 * T^2 + 0.2713 * T + 9.778.$$

Accordingly, the lactose solubility at 58° C., was calculated to be 35.6% (w/w). Therefore, the percentage insoluble lactose crystals will be the lactose concentration subtracted by the lactose solubility at 58° C. In this way, the percentage of the insoluble lactose crystals present in reaction system is calculated to be 19.4% (55% minus 35.6%) (w/w)

Typically, a suitable amount of lactose is added directly to a buffer solution at room temperature and heated to a desired reaction temperature. It is also possible to add lactose to water, followed by adjusting the pH of the lactose slurry to a working pH range of about pH3.5-7.5 that is within the enzyme activity range for example by adding caustic (NaOH) or a buffer solution.

The skilled people will realize that the optimum pH of individual immobilized beta-galactosidase depends on its source and the type of immobilization methods and that it might decrease during the enzymatic conversion. Consequently, the pH may need to be adjusted during the enzymatic conversion, e.g. by stepwise adding a caustic solution or via a pH start mode.

As mentioned above, in contrast to conventional methods employing highly concentrated lactose solutions, a method of the invention does not require extensive heating of lactose to completely dissolve the lactose. This not only reduces the energy consumption and thus operational costs that are associated with the heating step, but also avoids the undesirable color change of lactose solution to a more yellowish appearance.

However, practically, it might be also desired to dissolve the lactose completely, in order to remove the insoluble protein aggregates or insoluble mineral salt such as calcium phosphate or calcium citrate that may be present in the lactose crystals. Therefore, it is of course also possible to prepare a lactose slurry by heating a lactose feed to a high temperature ($T^1$) to dissolve lactose and remove the insoluble particles as mentioned above and cooling down to the desired reaction temperature ($T^2$) to let dissolved lactose crystallize out. As shown herein below, the heating of a completely solubilized lactose solution of >58% (w/w) followed by cooling to a temperature of about 60° C. resulted in the spontaneous crystallization of lactose.

The formation of good crystals and crystal growth are critical to the extraction and purification of lactose. α-lactose crystallizes from supersaturated solutions at temperatures below 93.5° C. to produce a variety of crystal shapes. The usual ones obtained resemble prism and tomahawk shapes, and are hard and only sparingly soluble. Above 93.5°

C., β-lactose crystallises out, usually as an uneven-sided diamond. A molecule of water is associated with the crystalline α-form of lactose and so it is referred to as the monohydrate. At temperatures over 120° C. and under vacuum, however, this water is lost and the highly hygroscopic α-lactose anhydride is formed. When lactose is dissolved in water, mutarotation occurs, ie. α- and β-anomers interconvert to produce a solution of 62.7% β-lactose at 20° C. As α-lactose is the far less soluble species, concentration of the solution results in α-lactose precipitating and further mutarotation takes place to maintain the same equilibrium position.

A method of the invention preferably comprises use of food grade or pharmaceutical grade lactose, or refined lactose that is between the food and pharmaceutical grade lactose. Food grade lactose is produced by concentrating whey or permeate (a co-product of whey protein concentrate production) to supersaturated solution and lactose crystallizes out, then removing and drying the lactose crystals. Special processes of crystallization, as well as grinding and fractionated sifting, produce types of lactose which differ in particle size distribution. Today, the industry offers several types of lactose ranging from superfine to extra coarse crystals for all applications. The lactose content is not less than 99%, with the sulfated ash content not more than 0.3%, both on a dry basis. The pH of a 10% solution is not less than 4.5 or more than 7.5.

To obtain a refined or a pharmaceutical grade of lactose, refining process is necessary. This involves redissolving the lactose crystals and treating the solution with virgin activated carbon, which absorbs a number of solutes including riboflavin and a variety of proteins. Also absorbed are a group of polypeptides known as protease peptones which are derived from β-casein. These peptones are produced by the action of plasmin, a protease enzyme which migrates from the bloodstream into the milk in the cow's udder. Further protein may be absorbed onto the activated carbon by temporarily adjusting the liquor pH. The carbon is removed by flocculation and filtration and then discarded. After crystallisation, subsequent separation of the crystals by centrifugation and cold water washing and drying, a high purity white pharmaceutical grade lactose is obtained. The crystals are milled or sifted to yield products with specific particle size distributions.

Following contacting the lactose slurry with a preparation comprising immobilized beta-galactosidase, the resulting reaction mixture is incubated under conditions favoring GOS synthesis. The skilled person will understand that the selected reaction temperature should both favor the GOS synthesis and the enzyme stability. Therefore, the optimum temperature is the temperature at which the immobilized enzyme can be recycled in economically optimal manner, for instance, disposing the immobilized enzyme when reaching the half-life of the immobilized enzyme at the individual selected immobilized beta-galactosidase. Typically, GOS synthesis is performed at a reaction temperature of between about 20 and about 60° C. In one embodiment, the reaction is carried out at 40-60° C., preferably 45-55° C., like at about 50° C.

The reaction mixture is incubated until the desired amount of GOS has been obtained. Depending on the incubation conditions and the amount of the immobilized enzyme used, GOS synthesis according to the invention is generally allowed to proceed from 0.5-100 hours. However, industrial production of GOS generally requires a rational integration with other units of operation involved, such as purification, demineralization, decoloration and the like. Thus, GOS synthesis at an industrial scale is preferably performed during a reaction period of at least 6 or 10 hours, preferably 12-36 hours for practical and economical reasons. For example, due to the high GOS yield and increased enzyme stability, a method of the invention is suitably practiced using an incubation time of about 18-24 hours. This allows for flexible accommodation in an employee working day while at the same time obviating the need for high amounts of enzyme, because a large amount of immobilized enzyme in the reactor will reduce the productivity and space-time yield For example, the dose of the immobilized beta-galactosidase can be used in an amount of up to 30 LU/gram initial lactose, preferably up to 25 LU/gram, more preferably in an amount of between about 10 and 20 LU/gram. As used herein, one lactase unit (LU) is defined as the quantity of enzyme that liberates 1 μmole of glucose per minute at the early stage of the reaction at 40° C., pH 6.0. When lactose is hydrolysed by lactase, it is converted into glucose and galactose. The lactase activity is determined by measuring the amount of liberated glucose.

There are several manners to perform GOS synthesis using a lactose "slurry" reaction as disclosed in the present invention. In a first embodiment, the slurry is placed in a separate reactor and the insoluble lactose crystals are retained by a microfilter. Then, the soluble lactose is pumped to a packed bed reactor (PBR) where the immobilized beta-galactosidase is located. The outlet of the PBR is returned back to the reactor. In this way, after certain time, the lactose will be completely dissolved and high GOS concentrations can be obtained.

In a second embodiment, lactose crystals are gradually added to the GOS solution. Lactose is dissolved and pumped to the PBR and the dissolved lactose will be converted to GOS.

In a third embodiment, not all the insoluble lactose crystals are added at once such that no difficulties with stirring the reaction mixture are encountered. For example, lactose crystals are directly added to an existing reaction mixture to replenish the initially present lactose crystals that have been dissolved and completely converted to GOS. Upon the visual detection of disappearance/dissolution of lactose crystals as the reaction proceeds, more lactose crystals can be added to continue the reaction until high, e.g. up to 75%, GOS solution can be obtained.

As will be understood, a method of the invention can be practiced using beta-galactosidase from a wide variety of sources, such as microorganisms, plants and animals. Microorganisms like bacteria, fungi and yeast are considered the preferred sources of beta-galactosidase for industrial applications. See ref Panesar 2010 for an overview of suitable microbial sources. Preferably, beta-galactosidase is isolated from a micro-organism selected from the group consisting of *A. oryzae, A. niger, B. circulans, S. singularis, T. aquaticus, K. lactis, K. marxianus* and *E. coli*. Some of the enzymes have high specificity to synthesize oligosaccharides of specific chain length and orientation of the linkage. For example, β-galactosidase sourced from *B. circulans* shows high specificity to β-1,4 linkages and in turn yields mainly β-1,4 linked galactosyl oligosaccharides (GOS) by transglycosylation, while β-galactosidase sourced from *Aspergillus oryzae* gives β-1,6 GOS mainly. Very good results were obtained with *B. circulans* beta-galactosidase, which is available from Daiwa Kasei, Amano, Japan in the form of the commercial enzyme preparation, Biolacta® N5.

A method of the invention is characterized by incubating a lactose slurry with immobilized beta-galactosidase. Various ways of enzyme immobilization are known in the art. They typically comprise a porous carrier onto which the beta-galactosidase is immobilized via covalent binding, via physical absorption (charge-charge or van der waals interaction), via gel encapsulation or a combination thereof. Table 2 of ref Panesar 2010 gives an overview of different sources of beta-galactosidase and methods of immobilization. Besides, the carrier-free immobilized enzymes such as CLEC (cross-linked enzyme crystals) or CLEAs (cross-linked enzyme aggregates) might be also applied [6,7].

The invention is not limited to any type of enzyme immobilization. However, carriers that can promote direct covalent binding of the enzyme are preferred, regarding the ease of operation and no leakage of the enzyme molecules into the reaction mixture.

As is shown herein below, good results were obtained with beta-galactosidase immobilized by covalent binding to a solid carrier. Preferably, the solid carrier is an activated acrylic polymer, preferably a functionalized polymethacrylate matrix. For example, a hexamethylenamino-functionalized polymethacrylate matrix (Sepabeads) or a macroporous acrylic epoxy-activated resin, like Eupergit C 250L, can be used.

After the reaction has proceeded to a desired level, GOS synthesis can be terminated by methods known in the art. For instance, the immobilized beta-galactosidase is physically separated from the remainder of the reaction mixture by filtration or by retaining the particles of the immobilized enzymes by a sieve installed on the bottom of the reactor.

As explained herein above, a method of the invention is advantageously used in a repeated batch operating system involving several consecutive batches ("cycles") of GOS synthesis. Furthermore, a method of the invention allows for the recycling of immobilized enzyme during several batches since detrimental effects of lactose crystallization during the GOS synthesis reaction are avoided by the use of a lactose slurry as lactose feed. This enables semi-continuous operation and multiple reuse of the enzyme.

Accordingly, in one embodiment a method further comprises, following a first cycle of GOS synthesis, the steps of: (a) washing the immobilized beta-galactosidase, (b) optionally storage of the washed immobilized beta-galactosidase until further use; and (c) one or more subsequent cycles of GOS synthesis by contacting the washed immobilized beta-galactosidase of step (a) with a lactose slurry such that the enzyme is recycled.

Prior to enzyme washing, it is typically physically separated from the GOS-containing reaction mixture. For example, if the enzyme used for GOS synthesis is used in a "tea-bag"-like pouch, the tea-bag can simply be taken out of the reaction mixture. Alternatively, GOS can be removed from the reactor while the immobilized enzyme remains in the reactor during washing.

For example, the enzyme is washed several times with demineralized water and/or the same buffer used in the GOS synthesis reaction. Immobilized enzyme can be sanitized e.g. to reduce the microbial count, by washing with an acetic acid solution of about pH 4.5. The enzyme may be stored in a buffer at a temperature below 10° C., preferably at around 4° C. Suitable buffers include those in the range of pH 5.5-7.5. For example, the enzyme is stored in 0.1M $K_2HPO_4/KH_2PO_4$ buffer, pH 6.0-7.0 at 4° C., prior to reuse. In one embodiment, a method of the invention comprises at least 5, preferably at least 8, more preferably at least 10 cycles of GOS synthesis employing recycled immobilized beta-galactosidase.

In a further aspect, the invention provides a composition comprising an aqueous slurry of crystalline lactose and comprising beta-galactosidase which is immobilized on a solid carrier. Preferred lactose concentrations, enzyme sources and enzyme concentrations are disclosed herein above.

EXPERIMENTAL SECTION

Figure 1:
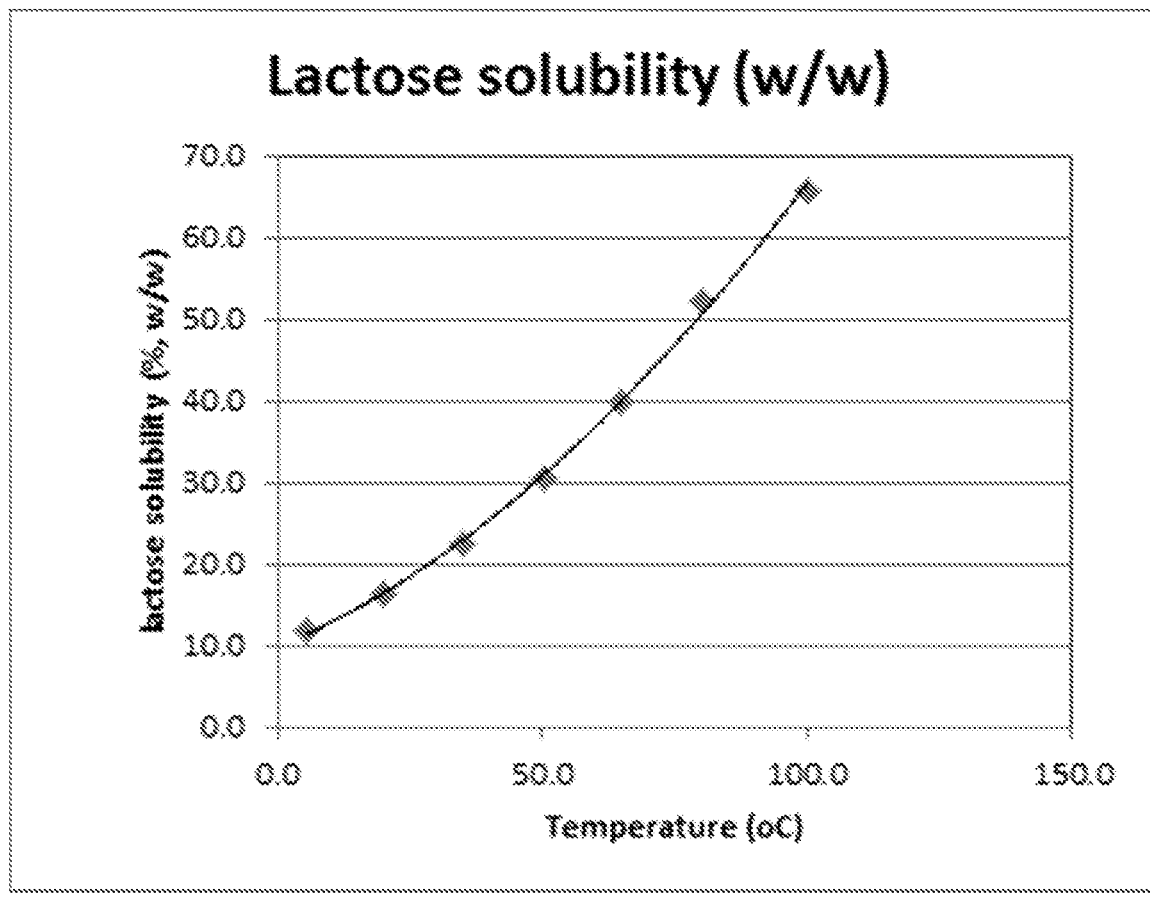
FIG. 1: Lactose solubility and temperature curve.
Figure 2:
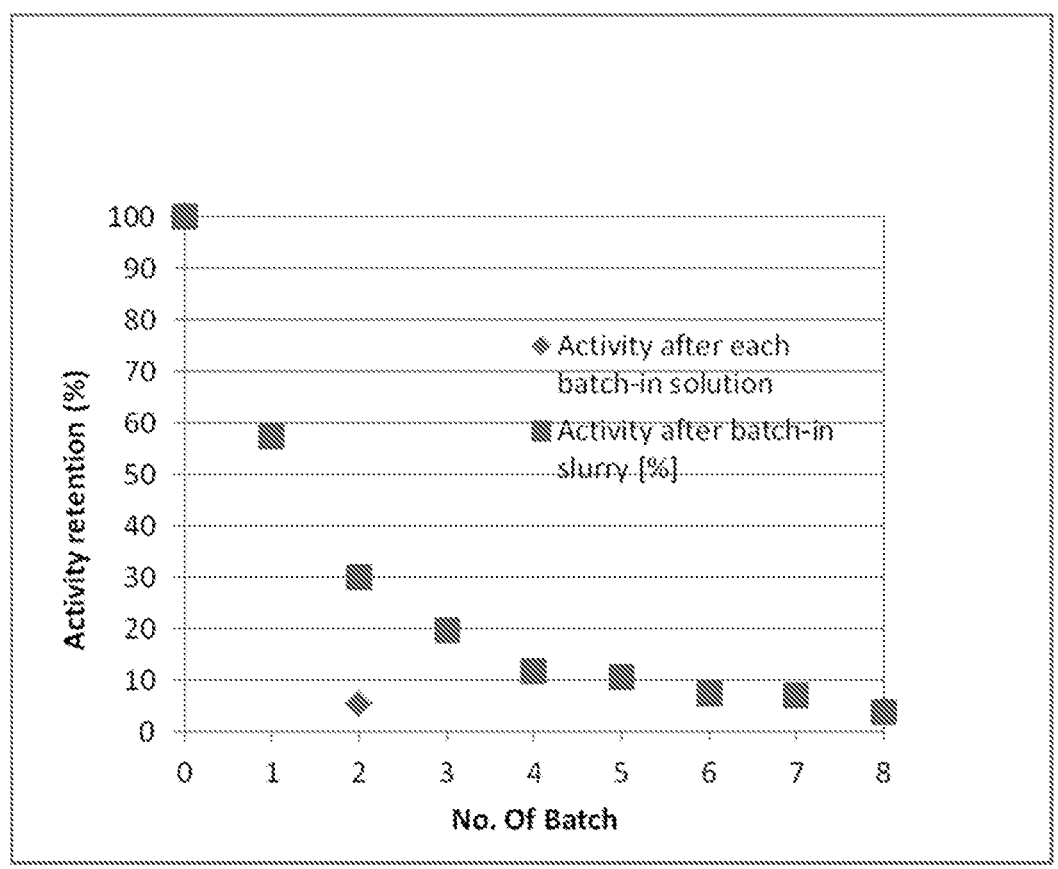
FIG. 2: Comparison of activity retention of immobilized beta-galactosidase EC-HA catalyzed GOS synthesis using a lactose slurry (■) or a lactose solution (♦) as lactose feed.

The examples herein below exemplify the advantageous effects of using a lactose slurry instead of a highly concentrated lactose solution in the manufacture of GOS using immobilized beta-galactosidase.

Example 1 (Comparative Example): Synthesis of GOS with Immobilized β-Galactosidase from *Bacillus Circulans* Using a Lactose Solution (55%)

Experimental Conditions:

35 gram lactose was added to 25 gram 0.1M $K_2HPO_4/KH_2PO_4$ buffer, pH 6.3 and was completely dissolved at 95° C. then cooled down to 58° C. Afterward, 2.7 gram carrier-bound enzyme immobilized on commercial carrier (Sepabeads EC-HA) via glutaraldehyde coupling with a specific activity of 131.16 LU/gram immobilized enzyme was added to initialize the enzymatic reaction. The enzyme dosage is 10.2 LU/gram lactose.

After 24 hours reaction time, the GOS was filtrated and the immobilized enzyme was washed with demineralized water and stored in 0.1M $K_2HPO_4/KH_2PO_4$ buffer, pH 6.0-7.0 at 4° C., prior to reuse.

Carbohydrates (galactose, glucose, lactose and GOS) were analyzed as previously described by Coulier et al. (J. Agric. Food Chem. 2009, 57, 8488-8495) and Warmerdam et al. (Appl Biochem Biotechnol (2013) 170:340-358).

The remaining enzyme activity and the GOS yield after the first batch and second batch was summarized in Table 1. Notably, the remaining activity of the immobilized enzyme was only 5.4% of the initial LU activity, suggesting that the immobilized enzyme was quickly denatured.

TABLE 1

A summary of GOS synthesis using immobilized beta-galactosidase in a completely solubilized lactose solution.

| Immobilized enzyme/ batch No. | Time [h] | GOS and sugar composition [% on dm] | | | | Activity retention after each batch [%] |
|---|---|---|---|---|---|---|
| | | Galactose | Glucose | Lactose | GOS | 100 |
| EC-HA - Batch 1 | 24 | 2.86 | 23.71 | 16.02 | 57.41 | 26.1 |
| EC-HA - Batch 2 | 24 | 1.39 | 21.27 | 28.13 | 49.21 | 5.4 |

Example 2 Synthesis of GOS with Immobilized
β-Galactosidase from *Bacillus Circulans* in a
Lactose Slurry (55% w/w) Reaction System of the
Invention Experimental Conditions:

70 gram lactose was added directly to 51 gram 0.1M $K_2HPO_4/KH_2PO_4$ buffer, pH 6. and subsequently the reaction mixture was heated to the reaction temperature 58° C. (and maintained for at least 1 hour) and 12 gram carrier-bound enzyme immobilized on commercial carrier (Sepabeads EC-HA) via glutaraldehyde coupling with a specific activity of 141.8 LU/gram immobilized enzyme) was added to initialize the enzymatic reaction. The enzyme dosage is 15.2 LU/gram lactose.

After 24 hours reaction time, the GOS was filtrated and the immobilized enzyme was washed with demineralized water and stored in 0.1M $K_2HPO_4/KH_2PO_4$ buffer, pH 6.0-7.0 solution at 4° C., prior to reuse.

TABLE 2

A summary of synthesis of GOS with immobilized
β-galactosidase from *Bacillus circulans* in
lactose slurry (55% w/w) in a consecutive mode

| Immobilized enzyme/ batch No. | Reaction time [h] | GOS and sugar composition [% on dm] | | | | LU Activity retention after batch [%] |
|---|---|---|---|---|---|---|
| | | Galactose | Glucose | Lactose | GOS | 100 |
| Batch 1 | 24 | 3.77 | 22.00 | 4.11 | 69.00 | 57.3 |
| Batch 2 | 24 | 5.31 | 24.46 | 3.44 | 65.38 | 30.1 |
| Batch 3 | 24 | 1.74 | 20.87 | 9.53 | 66.94 | 19.6 |
| Batch 4 | 24 | 1.28 | 18.88 | 12.03 | 67.03 | 11.7 |
| Batch 5 | 24 | 0.99 | 18.76 | 17.90 | 61.59 | 10.6 |
| Batch 6 | 24 | 0.74 | 18.16 | 25.77 | 54.59 | 7.3 |
| Batch 7 | 24 | 0.68 | 16.14 | 29.21 | 53.16 | 7.0 |
| Batch 8 | 24 | 0.65 | 16.54 | 32.63 | 48.93 | 3.8 |

Example 3 (Comparative Example): Synthesis of
GOS with Free β-Galactosidase from *Bacillus
Circulans* Using a Lactose Slurry (65%, w/w)
Reaction System Experimental Conditions:

85 gram lactose was added directly to 65 gram 0.1M $K_2HPO_4/KH_2PO_4$ buffer, pH 6. and subsequently the reaction mixture was heated to the reaction temperature 58° C. (and maintained for at least 1 hour) and 85 mg free beta-galactosidase of Biolacta N5 (Amano) dissolved in 2 ml demi water was added to initialize the reaction. The enzyme dosage is 5 LU/gram lactose.

The reaction mixture was incubated in a water batch with orbit shaker. After 24 hours reaction, the GOS content in the final reaction mixture was only 40% and there was still a lot of insoluble lactose left in the reaction mixture. This suggests that, in such a high lactose concentration slurry system, the free enzyme was less active than immobilized enzyme.

Example 4 Synthesis of GOS with Immobilised
β-Galactosidase from *Bacillus Circulans*
(Carrier-Epoxy Eupergit C 250 L) in Lactose
Slurry (65%, w/w) Reaction System 8 gram immobilized β-galactosidase of Biolacta N5 on Eupergit C 250 L was added to 200 gram lactose slurry with 20 mM potassium citrate buffer, pH7.0 and incubated at 60° C. The reaction mixture was stirred with a magnetic stirrer. The enzyme dosage was 7 LU/gram lactose.

After 24 hours, it was found that reaction mixture was completely clear and the GOS content was 57%.

This result suggests that a combination of high slurry concentration and immobilized enzyme is ideal for GOS synthesis at an industrial process; (i) there is no need to dissolve lactose completely, and (ii) less energy consumption for the concentration of the final product, when the concentration of the product from the reactor is also close to the concentration of the final product (GOS syrup, 75% (w/w)).

REFERENCES

1. Rivero-Urgell M and Santamaria-Orleans A (2001) Oligosaccharides: application in infant food. Early Human Development 65 Suppl. S43-S52
2. Torres D, Goncalves M, Teixeira J, Rodrigues L: Galacto-oligosaccharides: production, properties, applications, and significance as prebiotics. Compr Rev Food Sci, Food Safety 2010, 9:438-454.
3. Urrutiaa P, Mateob C, Guisan J M Wilson, Illanes L A (2013) Immobilization of *Bacillus circulans* β-galactosidase and its application in the synthesis of galacto-oligosaccharides under repeated-batch operation. Biochemical Engineering Journal 77:41-48
4. Panesar P S, Panesar R, Singh R S, Kennedy J F and Kumar H (2006) Microbial production, immobilization and applications of β-D-galactosidase. Journal of Chemical Technology and Biotechnology J Chem Technol Biotechnol 81:530-543
5. Grosova Z., Rosenberg M., Rebroŝ M. (2008) Perspectives and applications of immobilised β-galactosidase in food industry—a review. Czech J. Food Sci., 26: 1-14.
6. Gaur R, Pant H, Jain R, Khare S K: Galacto-oligosaccharide synthesis by immobilized β-galactosidase. Food Chem. 2006, 97, 426-430.
7. Cao L: Immobilized Enzymes. In Comprehensive Biotechnology (Second Edition) 2011, 2:461-476.

The invention claimed is:

1. A method for preparing galacto-oligosaccharides (GOS) from lactose, comprising
   (i) dissolving lactose crystals in an aqueous phase at room temperature to provide an aqueous slurry of crystallized lactose that contains at least 53% (w/w) lactose,
   (ii) heating said aqueous slurry of crystallized lactose from room temperature to a desired reaction temperature of between 20° C.-60° C.;
   (iii) contacting said heated aqueous slurry of crystallized lactose with *Bacillus circulans* beta-galactosidase immobilized on a porous carrier; and
   (iv) allowing for GOS synthesis, thereby preparing GOS from lactose.
2. The method according to claim 1, wherein said lactose is food grade or pharmaceutical grade lactose.
3. The method according to claim 1, wherein the pH of the aqueous slurry of crystallized lactose is pH 6.0-7.5.
4. The method according to claim 1, wherein GOS synthesis is performed at a temperature of between 40° C. and 60° C.
5. The method according to claim 1, wherein GOS synthesis is performed for at least 6 hours.

6. The method according to claim 1, wherein said immobilized beta-galactosidase is used in an amount of up to 30 LU/gram initial lactose.

7. The method according to claim 1, wherein said beta-galactosidase is immobilized on the porous carrier via covalent binding, via a charge-charge interaction or via gel encapsulation.

8. The method according to claim 7, wherein the porous carrier is an activated acrylic polymer carrier selected from the group consisting of a functionalized polymethacrylate matrix, a hexamethylenamino-functionalized polymethacrylate matrix or a macroporous acrylic epoxy-activated resin.

9. The method according to claim 1, further comprising, following a first cycle of GOS synthesis, the steps of:
   (a) washing the immobilized beta-galactosidase with water and/or buffer,
   (b) optionally storage of the washed immobilized beta-galactosidase until further use; and
   (c) at least one or more subsequent cycles of GOS synthesis using the washed immobilized beta-galactosidase of step (a) such that the immobilized enzyme is recycled.

10. The method according to claim 9, wherein the one or more subsequent cycles of GOS synthesis is at least 5 cycles of GOS synthesis.

11. The method according to claim 1, wherein the aqueous slurry of crystallized lactose contains at least 55% (w/w) lactose.

12. The method according to claim 5, wherein GOS synthesis is performed for 12-36 hours.

13. The method according to claim 6, wherein said immobilized beta-galactosidase is used in an amount of up to 25 LU/gram initial lactose.

14. The method according to claim 6, wherein said immobilized beta-galactosidase is used in an amount of between 10 and 20 LU/gram initial lactose.

* * * * *